(12) United States Patent
Hamzik et al.

(10) Patent No.: US 11,772,055 B2
(45) Date of Patent: Oct. 3, 2023

(54) LIGAND-MODIFIED FILTER AND METHODS FOR REDUCING METALS FROM LIQUID COMPOSITIONS

(71) Applicant: ENTEGRIS, INC., Billerica, MA (US)

(72) Inventors: James Hamzik, North Billerica, MA (US); Jad A. Jaber, Westford, MA (US); Nicholas J. Filipancic, Medford, MA (US); Justin Brewster, North Billerica, MA (US)

(73) Assignee: ENTEGRIS, INC., Billerica, MA (US)

( * ) Notice: Subject to any disclaimer, the term of this patent is extended or adjusted under 35 U.S.C. 154(b) by 113 days.

(21) Appl. No.: 17/184,273

(22) Filed: Feb. 24, 2021

(65) Prior Publication Data

US 2021/0260537 A1 Aug. 26, 2021

Related U.S. Application Data

(60) Provisional application No. 62/981,351, filed on Feb. 25, 2020.

(51) Int. Cl.
| | |
|---|---|
| *B01D 69/12* | (2006.01) |
| *B01D 71/26* | (2006.01) |
| *B01D 71/36* | (2006.01) |
| *B01D 71/58* | (2006.01) |
| *C02F 101/20* | (2006.01) |

(Continued)

(52) U.S. Cl.
CPC ............ *B01D 71/58* (2013.01); *B01D 69/12* (2013.01); *B01D 71/26* (2013.01); *B01D 71/36* (2013.01); *C02F 1/44* (2013.01); *C07C 229/16* (2013.01); *C08F 255/02* (2013.01); *C08F 259/08* (2013.01); *C02F 2101/203* (2013.01); *C02F 2101/22* (2013.01); *C02F 2103/346* (2013.01)

(58) Field of Classification Search
CPC ........ B01D 71/26; B01D 71/36; B01D 69/12; C02F 2101/203; C02F 2101/22; C02F 2103/346
See application file for complete search history.

(56) References Cited

U.S. PATENT DOCUMENTS 2,928,819 A * 3/1960 Noeske .................... C08F 8/20
525/344
4,690,766 A * 9/1987 Linder ............... B01D 67/0093
210/500.39

(Continued)

FOREIGN PATENT DOCUMENTS

| EP | 1215332 B1 | 7/2006 |
|---|---|---|
| JP | H0724314 A * | 1/1995 |

(Continued)

OTHER PUBLICATIONS

Hori Takahiro et al—JP-H0724314-A machine translation—1995 (Year: 1995).*

(Continued)

*Primary Examiner* — Bradley R Spies (57) ABSTRACT

Described are filter materials having polycarboxyl ligands, such as iminodiacetic acid, which are highly effective for filtering metals or metal ions from fluids. The filter materials can be particularly useful to filter various fluid compositions, such as those used for wet etching, removing photoresist, and cleaning steps in microelectronic device manufacturing.

19 Claims, 3 Drawing Sheets

(51) Int. Cl.
    *C02F 101/22*   (2006.01)
    *C02F 103/34*   (2006.01)
    *C02F 1/44*     (2023.01)
    *C07C 229/16*   (2006.01)
    *C08F 255/02*   (2006.01)
    *C08F 259/08*   (2006.01)

(56) References Cited

U.S. PATENT DOCUMENTS

| | | |
|---|---|---|
| 5,154,829 A | 10/1992 | Degen |
| 5,547,760 A | 8/1996 | Tarbet |
| 6,869,537 B1 | 3/2005 | Nambu |
| 9,855,534 B1 | 1/2018 | Ait-Haddou |
| 2005/0218068 A1 | 10/2005 | Komatsu |
| 2009/0039019 A1* | 2/2009 | Raman ............... B01D 69/147 |
| | | 210/490 |
| 2011/0259818 A1 | 10/2011 | Tamada |

FOREIGN PATENT DOCUMENTS

| | | |
|---|---|---|
| JP | 2004283710 A | 10/2004 |
| WO | 201705722 W | 1/2017 |

OTHER PUBLICATIONS

Panahi, H. A. et al., "Grafting of poly[1-(N,N-bis-carboxymethyl)amino-3-allylglycerol-cod imethylacrylamide] copolymer onto siliceous support for preconcentration and determination of lead (II) in human plasma and environmental samples", Journal of chromatography A, 2010, vol. 1217, No. 32, pp. 5165-5172.

Panahi, H. A. et al., "Iminodiacetic acid-containing polymer brushes grafted onto silica gel for preconcentration and determination of copper(II) in environmental samples", Journal of applied polymer science, 2012, vol. 126, No. 2, pp. 180-189.

* cited by examiner

LIGAND-MODIFIED FILTER AND METHODS FOR REDUCING METALS FROM LIQUID COMPOSITIONS

CROSS-REFERENCE TO RELATED APPLICATIONS

This application claims the benefit under 35 USC 119 of U.S. Provisional Patent Application No. 62/981,351 filed Feb. 25, 2020, the disclosure of which is hereby incorporated herein by reference in its entirety.

FIELD

The following description relates to ligand-modified articles, such as filter membranes, and to methods of using the articles for removing metals from liquid compositions.

BACKGROUND

Filters are used to remove unwanted materials from a flow of a useful fluid and have become important features in a wide variety of industrial technologies. Fluids that are treated to remove unwanted materials include water, liquid industrial solvents and processing fluids, industrial gases used for manufacturing or processing, and liquids that have medical or pharmaceutical uses. Unwanted materials that are removed from fluids include impurities and contaminants such as particles, microorganisms, and dissolved chemical species. Specific examples of filter applications include their use with liquid materials for semiconductor and microelectronic device manufacturing.

Filters can remove unwanted materials by a variety of different ways, such as by size exclusion or by chemical and/or physical interaction with material. Some filters are defined by a structural material providing a porous architecture to the filter, and the filter is able to trap particles of a size that are not able to pass through the pores. Some filters are defined by the ability of the structural material of the filter, or of a chemistry associated with the structural material, to associate and interact with materials that pass over the filter. For example, chemical features of the filter may enable association with unwanted materials from a stream that passes over the filter, trapping those unwanted materials such as by ionic, coordinative, chelation, or hydrogen-bonding interactions. Some filters can utilize both size exclusion and chemical interaction features to remove materials from a filtered stream.

In some cases, to perform a filtration function, a filter includes a filter membrane that is responsible for removing unwanted material from a fluid that passes through. The filter membrane may, as required, be in the form of a flat sheet, which may be wound (e.g., spirally), flat, pleated, or disk-shaped. The filter membrane may alternatively be in the form of a hollow fiber. The filter membrane can be contained within a housing or otherwise supported so that fluid that is being filtered enters through a filter inlet and is required to pass through the filter membrane before passing through a filter outlet.

The removal of ionic materials such as dissolved anions or cations from solutions is important in many industries, such as the microelectronics industry, where ionic contaminants and particles in very small concentrations can adversely affect the quality and performance of microprocessors and memory devices. In particular, it may be desirable to remove metal-containing materials such as metal ions from liquid compositions that are used for device fabrication. Metal-containing materials can be found in different types of liquids that are used for microelectronic manufacturing.

There remain various unresolved technical challenges for the removal of metal-containing materials from fluids. In the case of purification of photochemicals, especially complex multicomponent compositions containing solvents, resist polymers, quenchers, surfactants, and photo acid generators (PAGs), there is a need for greater selectivity for removal of certain metal contaminants in the presence of such other components in the formulation.

SUMMARY

This disclosure provides various inventive embodiments that are directed to removal of metal contaminants from fluids, as well as ligand-modified filter materials useful for carrying out such methods. The filters and methods of this disclosure are particularly effective for removal of metals from liquid compositions. Filtered liquid compositions with significantly reduced amounts of metals can be used in a microelectronic manufacturing process, such as liquids for removing photoresist or liquids used in acid etching. The ligand-modified filters, such as ligand-modified porous membranes, can be configured for use in a microelectronic manufacturing system, which can be utilized in the system as a point of use metal-removal feature for liquids entering the system.

Accordingly, one aspect of the disclosure provides a method for removing one or more metal(s) or metal ion(s) from a liquid composition. Thus, in this aspect there is provided a method of removing one or more metal(s) or metal ion(s) from a liquid composition, the method comprising:

contacting a filter material with a liquid composition comprising one or more metal or metal ions, the filter material possessing polycarboxyl ligands, wherein the polycarboxyl ligands are covalently bound to the filter material through at least one linkage which is other than through a carboxyl group, and reducing an amount of the one or more metal or metal ions in the liquid composition. In other words, the polycarboxyl pendant group or ligand is not bound to the filter material via, for example, an ester, amide, or imide bond. In contacting, the filter reduces an amount of the one or more metal or metal ions in the liquid composition.

In one embodiment, the polycarboxyl ligands are derived from iminodiacetic acid, ethylenediamine tetraacetic acid, 1,2-cyclohexanediamine-N,N,N',N'-tetraacetic acid, nitrilotriacetic acid, or iminodisuccinic acid.

"Polycarboxyl ligands" of the disclosure refer to chemical compounds having at least two carboxylic acid groups. In one embodiment, such compounds also possess at least one secondary or tertiary amine moiety. In one embodiment, such ligands possess the following partial structure:

wherein x is an integer of from 1 to 6, n is equal to 2 or 3, and z represents either a zero or +1 valence. In another embodiment, such ligands possess the following partial structure:

Examples of such polycarboxyl ligand compounds include those derived from iminodiacetic acid, ethylenediamine tetraacetic acid, iminodisuccinic acid, nitriloacetic acid, and the like. In a particular embodiment, the ligands this type are those derived from iminodiacetic acid.

Accordingly, in another embodiment, the method provides a method for manufacturing a microelectronic device. The method includes a step of performing filtering a liquid composition with the filter material comprising the polycarboxyl ligand as described herein. The metal- or metal ion-depleted liquid composition then contacts a microelectronic article in a step of manufacturing a microelectronic device.

In another embodiment, the disclosure provides a porous polymeric filter membrane that possesses a polycarboxyl ligand. The membrane is configured for use in conjunction with a microelectronic fabrication system, for providing a metal- or metal ion-depleted liquid composition to the device. The porous polymeric filter membrane can be arranged in a housing, such as a cartridge, and in fluid communication with a fluid source used for semiconductor manufacturing, such as supply containers that include a basic aqueous composition or an acidic aqueous composition. In certain embodiments, the porous polymeric filter membrane is a component of a microelectronic fabrication system.

Experimental studies associated with the current disclosure have revealed that filter materials with immobilized or pendant polycarboxyl ligands as described herein provide excellent reduction in the metal and/or metal ion contamination in fluid processing streams as compared to conventional ion-exchange ligands.

DETAILED DESCRIPTION

The disclosure illustrates various embodiments for methods of removing metal contaminants from fluids, wherein the ligand of the filter material possesses polycarboxyl ligands. Fluid composition can be passed through the ligand-modified filter material to effectively remove metal contaminants to levels suitable for a desired application. One application that can use the ligand-modified filter materials of the current disclosure is semiconductor manufacturing, such as for the purification of metals from solutions that are used for etching and cleaning semiconductor materials. Given the selectivity of their purification capabilities, the ligand-modified filter materials are particularly useful in photolithography in general, and in particular, in the practice of Extreme Ultraviolet Lithography (EUV) as well as immersion lithography.

A filter material on which the polycarboxyl ligand is attached, can be made of any suitable material or combination of materials. For example, exemplary filter materials can include one or more of a polymer, a metal, a ceramic, or a natural material. Further, in some aspects, the material of the filter can have a chemistry suitable for attachment to the polycarboxyl ligand. Alternatively, the surface of the filter material can be modified so that it is chemically reactive with the polycarboxyl ligand or a derivative thereof.

A "filter," refers to an article having a structure that includes filter material. For example, the filter can be in any useful form for a filtering process, including the form of a porous membrane, a bead, a tube, etc., the filter being made from one or more filter materials such as polymers, including synthetic and natural polymers, metal-containing materials, such as alloys, natural materials, ceramic, carbon fiber, etc. In some embodiments, the polycarboxyl ligand can be attached to the filter material.

The filter can be in any desired form suitable for a filtering application. Material that forms the filter can be a structural component of a filter itself and that provides the filter with a desired architecture. The filter can be porous or non-porous and can be of any desired shape or configuration. The filter per se can be a unitary article or can be represented by a plurality of individual articles, such as particles (e.g., resin beads).

In some embodiments, the filter material is formed from a polymeric material, a mixture of different polymeric materials, or a polymeric material and a non-polymeric material. Polymeric materials forming the filter can be crosslinked together to provide a filter structure with a desired degree of integrity.

Polymeric materials that can be used to form filter material of filters of the disclosure include hydrophobic polymers. In some embodiments, the filter material includes a polyolefin or a halogenated polymer. Exemplary polyolefins include polyethylene (PE), polypropylene (PP), polymethylpentene (PMP), polybutene (PB), polyisobutylene (PIB), and copolymers of two or more of ethylene, propylene, and butylene. In a further particular embodiment, filter material includes ultra-high molecular weight polyethylene (UPE). UPE filter materials, such as UPE membranes, are typically formed from a resin having a molecular weight (weight average molecular weight) greater than about $1 \times 10^6$ Daltons (Da), such as in the range of about $1 \times 10^6 - 9 \times 10^6$ Da, or $1.5 \times 10^6 - 9 \times 10^6$ Da. Crosslinking between polyolefin polymers such as polyethylene can be promoted by use of heat or crosslinking chemicals, such as peroxides (e.g., dicumyl peroxide or di-tert-butyl peroxide), silanes (e.g. trimethoxyvinylsilane), or azo ester compounds (e.g., 2,2'-azo-bis(2-acetoxy-propane). Exemplary halogenated polymers include polytetrafluoroethylene (PTFE), polychlorotrifluoro-ethylene (PCTFE), fluorinated ethylene polymer (FEP), polyhexafluoropropylene, and polyvinylidene fluoride (PVDF).

In other embodiments, the filter material includes a polymer selected from the group consisting of polyamide, polyimide, polysulfone, polyether-sulfone, polyarylsulfone polyamides, polyacrylates, polyesters, nylons, celluloses, cellulose esters, polycarbonates, or combinations thereof.

The polymeric material can be modified, in some modes of practice, to facilitate modification of the filter material with the polycarboxyl ligand. In certain embodiments, the polycarboxyl ligand includes at least one secondary or tertiary amine group which can facilitate attachment to a polymeric filter material. If the polymeric material is not inherently amine-reactive, it can be modified such as by halogenation or haloalkylation to provide a surface-reactive chemistry for the attachment of a polycarboxyl ligand. As noted herein, the polycarboxy ligand is however covalently bound to the filter material via linkage(s) which are other than carboxy linkages, such as esters, amides, and imides.

In some modes of practice, polymeric material of the filter is halogenated to provide amine-reactive sites. For example, polyethylene can be chlorinated by reacting gaseous chlorine at temperatures of greater than 50° C., optionally diluted with inert gas(es), with solid polyethylene powder (e.g., see U.S. Pat. No. 2,928,819, incorporated herein by reference).

In another mode of practice, the polymer of the filter material can be haloalkylated, such as chloromethylated. Chloromethylation is a known technique used for modifying polymers and generally uses a chloromethylation reagent (e.g., bis-chloromethyl ether (BCME); chloromethyl methyl ether (CMME); formaldehyde/methanol/hydrogen chloride/chlorosulfonic acid). Lewis acid and Friedel-Crafts catalysts, such as zinc chloride, zinc oxide, or ferric chloride, can be used with the chloromethylation reagents at elevated temperatures to modify the polymer (see, for example, US2003/0018091 (Pafford et al.) and WO2008/144115 (Harris et al.)). To provide the ligand of the disclosure on the filter, the haloalkyl group of the haloalkyl-modified filter material can be reacted with a polycarboxyl resulting in covalent bonding of ligand to the surface of the filter material.

In another mode of practice, the polycarboxyl ligand can be attached to a filter material through attachment with a reactive cross-linked coating. For example, the filter material can be coated with a composition comprising a monomer, oligomer, or polymeric material reactive with amines; such amine reactive polymers include poly(vinylbenzyl chloride), poly(epichlorohydrin), and epoxy resins. Other examples of reactive monomers include N,N'-methylenebis (acrylamide), triethylene glycol dimethacrylate, triethylene glycol diacrylate, and ethylene glycol divinyl ether. The coated filter material can then be cross-linked and the remaining reactive sites used for attachment of the desired ligand. For example, poly(vinylbenzyl chloride) can be dissolved in a suitable solvent, dried onto a porous membrane, cross-linked with a diamine, polyamine, or any other multifunctional reactive cross-linker, followed by attachment of an polycarboxyl ligand. Using a similar method, the cross-linking and ligand attachment can occur simultaneously. Alternatively, the amine reactive polymer can be (free-radical) crosslinked via irradiation or through use of photo-initiator crosslinking, followed by attachment of the amine containing ligand.

In another mode of practice, the ligand attachment can occur prior to coating on the filter material. For example, a polycarboxyl functionalized polymer can be prepared by reacting a polycarboxyl ligand or a reactive derivative thereof with a polymeric material having a functional group reactive with the amine of the ligand (such as poly(vinyllbenzyl chloride)). The filter material can then be coated with the resulting polycarboxyl ligand modified polymer and dried. Optional crosslinking techniques may also be used.

In another mode of practice, the filter material can be coated with the desired polycarboxyl ligand via monomer cross-linking. For example, the desired polycarboxyl ligand can be present in the form of a reactive monomer bearing acrylamide, vinyl, or other suitable unsaturated groups along with an epoxy functionality, suitable for reacting with an amine. Such compounds can be prepared by reacting, for example, iminodiacetic acid with glycidyl acrylate, glycidyl methacrylate, or allyl glycidyl ether. In the case of the reaction of iminodiacetic acid with allyl glycidyl ether, the resulting compound thus has both a pendant allyl group as well as two free carboxyl groups. The polycarboxyl containing monomers can be added to monomer formulations containing di-functional monomers, such as, N,N'-methylenebisacrylamide. These monomer formulations can also contain photo-initiators, such as, OMNIRAD 2959 (1-[4-(2-hydroxyethoxy)-phenyl]-2-hydroxy-2-methyl-1-propane-1-one). Once the membrane is imbibed with the resulting monomer solution, the membrane can be irradiated (ultraviolet, electron beam, gamma, etc.) to form a cross-linked coating with the desired polycarboxyl ligand incorporated into the coating (see, for example, WO2017/205722 (Jaber et al.)).

In another mode of practice, the desired polycarboxyl ligand can be attached to a filter material via grafting from the membrane. "Grafting" in this context can be accomplished by irradiation of the filter material in the presence of a photo-initiator and an unsaturated monomer containing the desired the polycarboxyl ligand (see, for example, WO2016/081729 A1 (Jaber et al.)). In another mode of practice, the filter material can be attached with the desired polycarboxyl ligand via grafting from the membrane using electron beam or gamma irradiation. Grafting using electron beam or gamma irradiation can be accomplished using techniques known as pre-irradiation grafting or simultaneous irradiation grafting.

In another mode of practice, the filter material can be embedded with resin particles to form a hybrid particle/membrane filter material. For example, porous poly(styrene-co-divinylbenzene) resin particles having the desired polycarboxyl ligand attached can be introduced to a polymer mixture used for membrane extrusion or membrane casting. Using this method, the resulting porous polymeric membrane would have embedded porous particles with the desired polycarboxyl ligand attached. In some embodiments, the resulting membrane can have a tight particle retentive membrane placed downstream of the porous particle containing membrane (see, for example, US 2009/0039019 A1 (Raman)).

The concentration of polycarboxyl ligand can be sufficient to allow the ligand to be immobilized on a surface of the filter material at a desired density. A ligand solution can be applied to surfaces of filter material by any useful technique, such as by spraying, submerging, soaking the filter material solution, or the like. Desirably, the entire surface of the filter can be contacted with the solution, such as all internal surfaces of a porous filter membrane. If necessary, the application step may include manipulation of the filter material, e.g., by rolling or squeezing a porous filter medium to cause wetting of all surfaces of the porous filter.

In various examples of methods and devices of the present description, the filter includes a porous filter membrane with the polycarboxyl ligand attached to material that forms the membrane. As used herein, a "porous filter membrane" is a porous solid that contains porous (e.g., microporous) interconnecting passages that extend from one surface of the membrane to an opposite surface of the membrane. The passages generally provide tortuous tunnels or paths through which a liquid being filtered must pass. Metal species of sizes small enough to pass through the pores of the membrane can be trapped on the membrane by interaction with the polycarboxyl ligand, such as by a chelation interaction between the ligand and the metal. This is referred to as a "non-sieving filtration mechanism."

The filter can also function to prevent any particles (e.g., metal containing particles) present within the liquid that are larger than the pores from entering the microporous membrane or can function to trap the particles within the pores of the microporous membrane (i.e., wherein particles are removed by a sieving-type filtration mechanism). The liquid to be treated can pass through the membrane resulting in flow-through having a reduced amount of metals, such as a reduced amount of ionic metal species, a reduced amount of metal-containing particulates, or both.

Accordingly, a porous polymeric membrane on which the polycarboxyl ligand is attached can remove metal and metal ion contaminants in a solution that is passing through the membrane, as well as any material that is of a size too large to pass through the pores of the membrane.

Porous membranes of the disclosure can be described with reference to one or more properties of the membrane. Example porous polymeric filter membranes as described herein can be characterized by physical features that include pore size, bubble point, and porosity. For example, the membrane can be described in terms of bubble point, which is commonly used to reflect pore size.

The bubble point method is based on the premise that, for a particular fluid and pore size with constant wetting, the pressure needed to force an air bubble through the pore is in inverse proportion to the size of the hole. The diameter of the capillary can be calculated by determining the pressure required to force water out of the capillary. Methods for determining bubble point can include wetting the membrane, applying pressure to the membrane, and then determining at what pressure point bubbles are emitted from the upper surface of the membrane. A standard method for a bubble-point is set forth in American Society for Testing and Materials Standard (ASMT) Method F316. In certain aspects of the disclosure, the porous polymeric membrane can have a bubble point in the range of from about 2 psi to about 400 psi, about 4 psi to about 200, or about 4 psi to about 160 psi, when ethoxy-nonafluorobutane (HFE-7200) is used as the wetting solvent, and at a temperature of 20-25 degrees Celsius.

Alternatively, pore size can be measured by known techniques such as by Mercury Porosimetry (MP), Scanning Electron Microscopy (SEM), Liquid Displacement (LLDP), or Atomic Force Microscopy (AFM).

The porous polymeric filter membrane can have any pore size that will allow the filter membrane to be effective for performing as a filter membrane. The pore size can be correlated with bubble point determination. In some embodiments, porous membranes can have an average pore size in a range of from about 0.001 microns to about 5 or 10 microns, e.g., from 0.01 to 0.8 microns. The average pore size can be selected based on one or more factors that include: fluid flow rate, pressure, pressure drop considerations, viscosity considerations, impurities in the liquid to be treated (such as amount of metal impurities), and any particle size of the impurities.

Further, the disclosure contemplates use of polymeric membranes with generally uniform pore sizes resulting from a higher degree of pore symmetry, as well as membranes with non-uniform pore sizes (variable pore diameters) resulting from pore asymmetry. Pores can be isotropic or anisotropic, skinned or unskinned, symmetric or asymmetric, and any combination of these.

A porous polymer filter layer as described may have any porosity that will allow the porous polymer filter layer to be effective as described herein. Example porous polymer filter layers can have a relatively high porosity, for example a porosity of at least 60, 70 or 80 percent. As used herein, and in the art of porous bodies, a "porosity" of a porous body (also sometimes referred to as void fraction) is a measure of the void (i.e., "empty") space in the body as a percent of the total volume of the body, and is calculated as a fraction of the volume of voids of the body over the total volume of the body. A body that has zero percent porosity is completely solid.

The filter membranes described herein can be useful with any type of industrial process that requires a high purity liquid material as an input. Non-limiting examples of such processes include processes of preparing microelectronic or semiconductor devices, a specific example of which is a method of filtering liquid process material used for semiconductor photolithography. The filters of the present disclosure can remove metal ions and metal-containing particulates from a process liquid or solvent used for preparing microelectronics or semiconductors and may also remove other non-metal particulate material by the sieving action of the membrane. The filters of the present disclosure are surprisingly selective in the removal of undesired metal ions from such a liquid material while not affecting other materials typically found in more complex photoresist compositions, such as solvents, resist polymers, quenchers, surfactants, and photo acid generators (PAGs). This property of selectivity can be represented as "sensitivity shift". The benefit observed by the filter media described herein is that there is almost no shift in sensitivity, i.e., no change in the width of the patterns on the silicon wafer when one compares patterns created from a resist formulation comprising PAG filtered through metal removal filters described herein to a resist formulation with non-filtered PAG. Purasol™ filtration systems, for example, can remove metal contamination but can also bind PAG molecules, resulting in a sensitivity shift. The ligand modified filter media described herein exhibits greater selectivity insofar as it removes metal contamination without binding PAG molecules, thereby resulting in cleaner solution (i.e., reduced metal contamination) with a greatly reduced sensitivity shift.

Porous membranes of the disclosure can be of any desired geometric configurations suitable for use in a system for reducing metal or metal ion contamination in a fluid stream. For example, the porous membranes described herein can have any one or more of a variety of geometric configurations or forms. For example, the porous membrane can have any one or more shapes selected from circular, semi-circular, oval, semi-oval, or polygonal such as square, rectangular, hexagonal, or octagonal, etc. The porous membrane can be in the form of a flat sheet, a corrugated sheet, a pleated sheet, and a hollow fiber, among others.

A porous polymeric filter membrane as described can be in the form of a sheet or hollow fiber having any useful thickness, e.g., a thickness in a range from 20 to 400 microns, e.g., from 40 or 80 to 100 or 200 microns.

The polycarboxyl ligand can also be immobilized on filter material that is in the form of filter particles. The filter particles can be referred to as "resins," or "polymeric resins" and can be formed by precipitation, grinding, or milling, such as to form resin particles with sizes in the range of about 5 to about 600 microns, or about 8 to about 75 microns, or about 8 to about 20 microns. The distribution of particle sizes can vary; however, in some embodiments it can be less than about ±25%, in other embodiments it can be less than about ±10%.

Porous membranes of the disclosure can be associated with a support structure, a housing, or both. For example, the coated porous membrane can be supported by a frame, bracket, clip, web, net, and cage, and the like. In some constructions, at least part of the support structure can be a housing, as described herein. Alternatively, the porous membrane is unsupported.

The porous membrane can be present as a part of a filter assembly that includes a housing. For example, the housing is fluidically sealed (aside from inlet and outlet ports) and able to hold a volume of liquid and configured to allow the liquid to pass through the membrane. A housing can be used to form a larger filter structure such as a filter assembly (single or multilayer) or a filter cartridge that is used in a filtering system. The filtering system will place the filter membrane, e.g., as part of a filter assembly or as part of a filter cartridge, in a filter housing to expose the filter membrane to a flow path of a liquid chemical to cause at least a portion of the flow of the liquid chemical to pass through the filter membrane, so that the filter membrane removes an amount of the impurities or contaminants from the liquid chemical. The structure of a filter assembly or filter cartridge may include one or more of various additional materials and structures that support the composite filter membrane within the filter assembly or filter cartridge to cause fluid to flow from a filter inlet, through the filter material (e.g., filter membrane), and through a filter outlet. The filter membrane supported by the filter assembly or filter cartridge can be in any useful shape, e.g., a pleated cylinder, a cylindrical pad, one or more non-pleated (flat) cylindrical sheets, a pleated sheet, among others.

Figure 1:
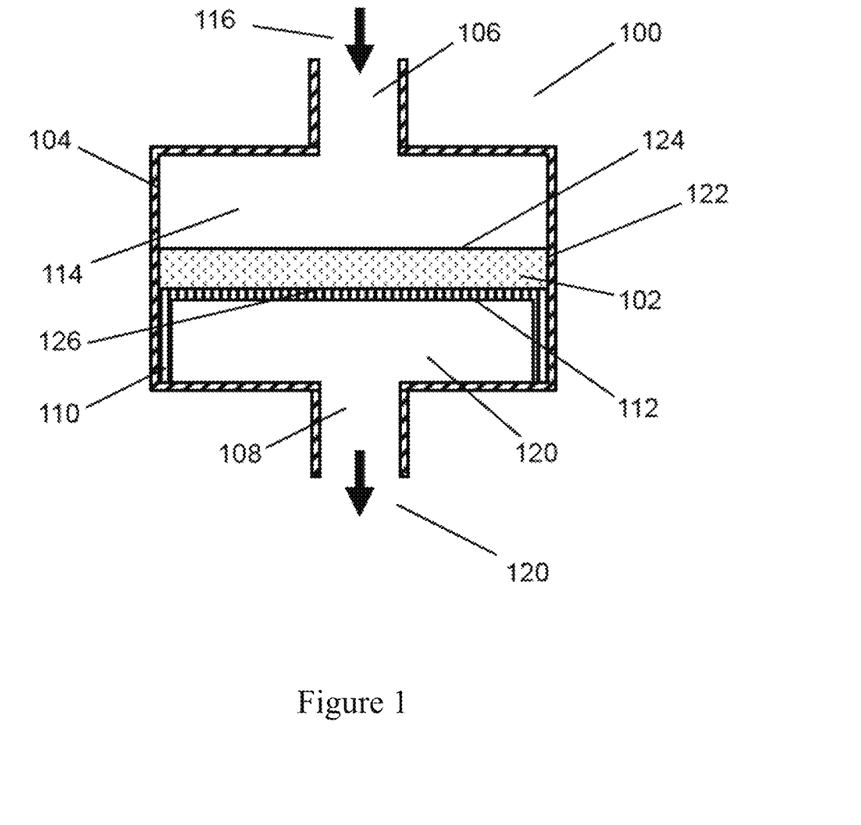
FIG. 1 is an illustration of an exemplary cross-section of a filter with a single porous membrane having a ligand of the disclosure.

An embodiment of the disclosure includes a filter device and a method of removing metal contaminants from a liquid, such as a base-containing liquid or an acid-containing liquid, wherein the liquid is passed through a porous polymeric membrane that has the polycarboxyl ligand. As shown in FIG. 1, the disclosure provides a filter 100 that includes a porous polymeric membrane 102. The porous polymeric membrane 102 includes a polycarboxyl ligand immobilized on a surface of the membrane. The filter 100 can have a housing 104 that provides a structure to the filter 100 and that fluidically seals an internal portion of the filter. The housing 104 can be any shape and size, such as cylindrical, polygonal, etc.

One portion of the filter can include an inlet port 106, to receive a metal/metal ion-containing fluid composition to be filtered. The inlet port 106 can be configured to be connected to a fluid supply line. As such, the inlet port 106 can include a valve, a gasket, etc. (not shown) to facilitate connection to a fluid supply. The metal/metal ion-containing fluid composition to be filtered can flow through inlet port 106 in direction indicated by arrow 116, and into a headspace 114 in the filter 100, as defined by an input-facing surface 124 of porous polymeric membrane 102, the internal surface of the housing 104, and the inlet port 106. In embodiments, the filter can be constructed so the headspace has a volume that is a desired percentage of the total internal volume of the filter.

The internal portion of the filter can include the porous membrane in any suitable placement or arrangement, with FIG. 1 showing the porous polymeric membrane 102 having a disc-like architecture (a cross-sectional view is shown). A side 122 of the porous polymeric membrane 102, such as the outer circumference of the membrane, can be in contact with the inner surface of the housing 104. The porous polymeric membrane 102 can also have an input-facing surface 124, which first contacts the metal/metal ion-containing fluid, and an output-facing surface 126, from which treated fluid with reduced amounts of metal/metal ions flow. Aspects of the filter can optionally be described in terms of the range of the ratio of the surface area of the input-facing surface 124 to the volume of the porous polymeric membrane 102, or the ratio of the surface area to the thickness of the filter.

The filter 100 can also include one or more features that support the porous polymeric membrane 102 within the filter. Any arrangement for supporting the filter can be used and can include one or more distinct structural feature(s), such as a frame, frame, bracket, clip, web, net, and cage, and the like, or a material such as an adhesive can be used to support the membrane. A combination of an adhesive and a structural supporting feature can be used. In an embodiment, and with reference to FIG. 1, the filter includes a frame having frame portions 110 and 112, with frame portion 110 in contact with the inner surface of the housing 104, which is attached to portion 112. Portion 112 can be in contact with the output-facing surface 124 of the porous polymeric membrane 102 and can provide support to the membrane during filtering. Frame portion 112 can have a grid-like structure to freely allow filtered liquid to pass into the backspace 120 of the filter, while still providing structural support to the polymeric porous membrane under increased fluidic pressures.

In use, a liquid enters the filter through inlet port 106 in direction indicated by arrow 116, and then fills the headspace 114 within the filter 100. Sufficient fluidic pressure is applied to cause the fluid to move through the porous polymeric membrane at a desired flow rate.

Exemplary flow rates for porous membranes are in the range of about 0.1 L/min to about 40 L/min, or more preferably about 5 L/min to about 20 L/min. Alternatively, the flow rate for a porous membrane is expressed in terms of the amount of liquid flowed per area of the filter per time (e.g., Liter/m$^2$/h=LMH), such as about 100 LMH/bar to about 30,000 LMH/bar, or more preferably about 5,000 LMH/bar to about 15,000 LMH/bar.

In some embodiments, the filter of the disclosure includes a composite membrane arrangement. For example, a filter with a composite membrane can include two or more filter materials, such as two or more filter articles. For example, the filter can include a first porous polymeric membrane that includes one of the polycarboxyl ligand, and a second filter material that does not include the ligand present in the first porous polymeric membrane (i.e., a different polycarboxyl ligand or some other ligand) or that is in some way different from the first porous polymeric membrane. The second filter material can also be in the form of a porous membrane, or can be different, such as having a non-porous form. The second filter material can be made of the same or of a different polymeric material than the first membrane, and can either be modified, such as modified with a ligand not present in the first membrane (e.g., the polycarboxyl ligand), or unmodified.

In some embodiments, the filter includes a first porous polymeric membrane that includes the polycarboxyl ligand, and a second porous polymeric membrane that includes a different polycarboxyl ligand. In other embodiments, the filter includes a first porous polymeric membrane that includes the polycarboxyl ligand, and a second porous polymeric membrane that includes either no polycarboxyl ligand, or a different polycarboxyl ligand. In embodiments, the first and second porous polymeric membranes are constructed from the same or a similar polymeric material and have the same or a similar pore size. In other embodiments, the first and second porous polymeric membranes are constructed from the different polymeric materials and/or have different pore sizes.

In some embodiments, porous resin particles with the desired polycarboxyl ligand attached can be in the form of a packed bed and placed upstream of a retentive filter. The packed resin bed can be in the form of a mixed particle bed. For example, porous poly(styrene-co-divinylbenzene) resin particles with the desired polycarboxyl ligand can be mixed with porous poly(styrene-co-divinylbenzene) resin particles with the desired polycarboxyl attached and the mixture of resin particles can be placed in a packed resin bed upstream if a retentive filter. In some embodiments, the downstream retentive filter can be a membrane that is surface modified, hydrophilic, or with a ligand attached. In some embodiments, the retentive filter can be pleated, spiral wound, or layered and the porous resin particles can be packed into the flow path upstream of the retentive filter.

The filter of the disclosure as described can be useful for filtering a liquid to remove undesired metal-containing material (e.g., contaminants or impurities) from the liquid to produce a high purity liquid that can be used as a material of an industrial process. In particular, a porous polymeric filter membrane can be useful to remove a dissolved and/or suspended metal containing contaminant(s) from a liquid that is flowed through the membrane using a combination of a sieving mechanism and ligand binding of the metal ions. That is, larger metal-containing particles can be trapped by the filter by size restriction according to pore size, and metal ions which otherwise can travel through the pores, are captured by interaction with the polycarboxyl ligand immobilized on the membrane.

The filter material(s) including the polycarboxyl ligand can be used to remove metals and metal ions from fluids having levels of these materials that are too high for desired processes.

Exemplary metals that can be removed from the fluids using the ligand-modified filter materials of the disclosure include alkali metals which include the following chemical elements in group 1 of the periodic table: lithium (Li), sodium (Na), potassium (K), rubidium (Rb), and cesium (Cs). Other exemplary metals that can be removed from the fluids using the ligand-modified filter materials of the disclosure include alkaline earth metals which are the following chemical elements in group 2 of the periodic table: beryllium (Be), magnesium (Mg), calcium (Ca), strontium (Sr), barium (Ba), and radium (Ra). Other exemplary metals that can be removed from the fluids using the ligand-modified filter materials of the disclosure include transition metal which are elements in the d-block of the periodic table, which includes groups 3 to 12 on the periodic table, and include, but are not limited to transitions metals such as titanium (Ti), vanadium (V), chromium (Cr), manganese (Mn), iron (Fe), cobalt (Co), nickel (Ni), copper (Cu), zinc (Zn), yttrium (Y), zirconium (Zr), molybdenum (Mo), ruthenium (Ru), palladium (Pb), silver (Au), cadmium (Cd), tungsten (W), and mercury (Hg). Other exemplary metals that can be removed from the fluids using the ligand-modified filter materials of the disclosure include post transition metals (groups 13-15), which include aluminum (Al), gallium (Ga), indium (In), tin (Sn), thallium (Tl), lead (Pb), and bismuth (Bi). In one embodiment, the polycarboxyl ligand-modified filters described herein preferentially remove substantially all of the iron and zinc from such solutions.

Metal contaminant can refer to neutral, negatively charged, or positively charged metal species and combinations thereof which may be present at equilibrium. The metals can be in the liquid in the form of dissolved ions, suspended charged particles, colloids, or other aggregates, and any of these metal forms can be removed from the fluids using the ligand-modified filter materials of the disclosure include. Several metal ions, for example Fe and Al, can exist as oxides in water. These kinds of ions can form amphoteric colloidal particles or complexes. In basic conditions, such as base cleaning solution (SC1), some of the metal ions can exits as hydroxides, oxides, oxyhydroxides, and other anions, or any combination of these. In some fluids, metal ions may form species that are amphoteric and can include one or more of these groups and these can exist as either cationic or anionic complexes depending upon the conditions (pH, temperature, ionic strength) of the fluid.

Metal ionic impurities in a variety of fluids may be detected using ion chromatography. The removal of metal material from a fluid treated by the filters of the disclosure can be also determined using inductively coupled plasma mass spectrometry (ICP-MS).

A filter membrane of the present description can be useful with any type of industrial process that requires a high purity liquid material as an input. Non-limiting examples of such processes include processes of preparing microelectronic or semiconductor devices, processes of preparing pharmaceutical compositions, and diagnostic (e.g., medical diagnostic) compositions and methods. Methods and filters of the disclosure can be used in any of these areas.

A specific example is a method of filtering a liquid process material used for semiconductor photolithography. Examples of contaminants present in a process liquid or used for preparing microelectronic or semiconductor devices may include metal ions dissolved in the liquid, solid particulates suspended in the liquid, and gelled or coagulated materials (e.g., generated during photolithography) present in the liquid. In embodiments, the methods and filters of the disclosure are used to provide purified, low metal containing liquid compositions for front-end cleaning tools which are used to create the foundation for an integrated circuit. For example, the filters of the disclosure can be used to purify cleaning and etching agents, to minimize product contamination and improve process efficiencies (such as etch rate). In chemical-mechanical polishing processes, water is used in addition to reagents and abrasive particles.

In another mode of practice, the ligand modified filters are used to remove metal and metal ion contaminants from an organic solvent. Some specific, non-limiting, examples of solvents that can be filtered using a filter membrane as described include: n-butyl acetate (nBA), isopropyl alcohol (IPA), 2-ethoxyethyl acetate (2EEA), a xylene, cyclohexanone, ethyl lactate, isopentyl ether, methyl-2-hydroxyisobutyrate, methyl isobutyl carbinol (MIBC), methyl isobutyl ketone (MIBK), isoamyl acetate, undecane, propylene glycol methyl ether (PGME), propylene glycol monomethyl ether acetate (PGMEA), and a mixed solution of propylene glycol monomethyl ether (PGME) and PGMEA (7:3) mixing ratio surface tension of 27.7 mN/m).

For example, in some modes of practice, a solvent is obtained having an amount of metal ion and/or metal containing impurities that are higher than desired for a target application, such as cleaning solvents, or solvents for resist stripping applications in lithography, for formation of an integrated circuit. For example, the metal impurities can be present in a total amount of greater than 0.001 µg/L (1000 parts per trillion (ppt)), greater than 0.005 µg/L (5000 ppt), greater than 0.01 µg/L (10,000 ppt). or greater than 0.05 µg/L (50,000 ppt) in the solvent. The solvent is then passed through the filter that includes the polycarboxyl ligand to remove metal contaminants and to provide a filtered solvent having an amount of metals that is lower than the amount of metals in the starting solvent. In modes of practice the filter of the disclosure can remove an amount of about 25% (wt) or greater, about 30% (wt) or greater, about 35% (wt) or greater, about 40% (wt) or greater, about 45% (wt) or greater, about 50% (wt) or greater, about 55% (wt) or greater, about 60% (wt) or greater, about 65% (wt) or greater, about 70% (wt) or greater, about 75% (wt) or greater, about 80% (wt) or greater, about 85% (wt) or greater, about 90% (wt) or greater, or about 95% (wt) or greater, any one or more metals from the starting solvent.

The solvents that are treated to remove metal contaminants can be passed through the filters under desired conditions, such as those that enhance removal of metal contaminant from the fluid stream. In some modes of practice, the solvent is passed through the filter at a temperature of about 160° C. or less, 120° C. or less, or 80° C. or less.

The passage of solvent through the porous membrane that includes polycarboxyl ligand is not limited to any particular flow rate provided an essentially flux-independent metal impurity removal is achieved and a useful pressure drop for the application is provided. The area of the porous membrane used can be chosen to provide a device with an acceptable pressure drop and essentially flux independent ligand binding for the flow rate and process requirements of the application. In various embodiments, the membrane area can be about 0.25 cm$^2$ or greater, and the specified or fixed area used to determine pressure drop for each membrane to meet the requirements of the application.

In some modes of practice, filters including porous membrane of the disclosure can remove particulates, metal-containing or other, from the fluid stream. Particle retention can be evaluated by measuring the number of test particles removed from a fluid stream by a membrane placed in the fluid stream. By one method, particle retention can be measured by passing a sufficient amount of an aqueous feed solution of 0.1% Triton™ X-100 (available from Dow), containing 8 ppm polystyrene particles (0.025 µm Green Fluorescent Polymer Microspheres, Fluoro-Max (available from ThermoFisher Scientific), to achieve 0.5, 1, and 2% monolayer coverage through the membrane at a constant flow of 7 milliliters per minute, and collecting the permeate. The concentration of the polystyrene particles in the permeate can be calculated from the absorbance of the permeate. Particle retention is then calculated using the following equation:

$$\text{particle retention} = \frac{[\text{feed}] - [\text{filtrate}]}{[\text{feed}]} \times 100\%.$$

In addition, a filter membrane as described can be characterized by a flow rate or flux of a flow of liquid through the filter membrane. The flow rate must be sufficiently high to allow the filter membrane to be efficient and effective for filtering a flow of fluid through the filter membrane. A flow rate, or as alternately considered, a resistance to a flow of liquid through a filter membrane, can be measured in terms of flow rate or flow time (which is an inverse to flow rate). A filter membrane as described herein including the polycarboxyl ligand can in certain embodiments have a relatively low flow time, for example in combination with a bubble point that is relatively high, and good filtering performance (e.g., as measured by particle retention). An example of a useful or preferred flow time can be below about 8,000 seconds/500 mL, e.g., below about 4,000/500 mL, below about 2,000 seconds/500 mL, below about 1,000 seconds/500 mL, below about 500 seconds/500 mL, or below about 200 seconds/500 mL.

Membrane water flow time can be determined by cutting membranes into 47 mm disks and wetting with water before placing the disk in a filter holder attached to a reservoir for holding a volume of water. The reservoir is connected to a pressure regulator. Water is flowed through the membrane under 14.2 psi (pounds per square inch) differential pressure. After equilibrium is achieved, the time for 500 mL of water to flow through the membrane is recorded.

EXAMPLES

Example 1

Preparation of 0.2 um Pore Size UPE Membrane with IDA Ligand

A monomer solution was prepared by combining 3.5% IDA (iminodiacetic acid), 3% allyl glycidyl ether, 5% sodium hydroxide, and 88.5% deionized water. The monomer solution was heated at 45° C. overnight with gentle stirring to result in a solution containing a vinyl iminodiacetic monomer. Next, a UV active IDA coating solution was prepared by adding 0.22% of a photo-initiator, IRGACURE® 2959, and 1.45% of a crosslinker, N,N'-methylenebis(acrylamide), to the solution containing the vinyl IDA monomer and mixing at room temperature till a homogeneous solution was obtained.

A 47 mm disk of 0.2 µM pore size UPE (ultrahigh molecular weight) membrane, commercially available from Entegris, Inc. was wet with IPA solution for 25 sec, exchanged into deionized water, and submerged into the UV active IDA coating solution. The membrane disk was removed and placed between polyethylene sheets and the excess liquid and air was displaced by applying pressure with a rubber roller. The polyethylene sheets containing the 0.2 um pore size UPE membrane imbibed with the UV active IDA coating solution was exposed to UV by transporting it through a Fusion UV Systems, Inc. broadband UV at 10 ft per minute. After emerging from the UV unit, the resulting IDA ligand coated membrane was removed from the polyethylene sheets and immediately washed in deionized water. Next, the IDA ligand coated membrane was further washed by submerging in methanol for 5 minutes, and finally, dried on a restraining holder in an oven at 65° C. for 10 min.

Example 2

A membrane disk prepared according to Example 1 was cleaned using the following process. First, the 47 mm membrane disc was placed into a clean 30 ml PTFE vial (Savillex) and the membrane was wetted with 20 mL IPA (Isopropanol Gigabit®, KMG) for 1 min and the IPA was decanted. Next, the membrane was exposed to 20 mL of a mixture of 70% IPA/10% HCl (Hydrochloric Acid 37% Gigabit®, KMG) and gently agitated for 1 hour. After an hour the 70% IPA/10% HCl solution was decanted. Next, the membrane was washed and exchanged into de-ionized water (DIW) several times, and the DIW was decanted. Next, the membrane was exposed to an additional 20 mL of 70% IPA/10% HCl solution and gently agitated for 16 hours. After 16 hours, the 70% IPA/10% HCl was decanted. Next, the membrane was washed and exchanged into DIW several times, and the DIW was decanted. Next, the membrane was exchanged into 20 mL of 2% NH$_4$OH (Ammonium Hydroxide 29% Cleanroom® MB, KMG) and gently agitated for 1 hour. Finally, the membrane was exchanged several times with DIW followed by IPA and placed in a convection oven at 70° C. till dry. The cleaned membrane was placed in a clean PTFE jar to await use.

Example 3

An IDA-modified UPE membrane disc prepared according to Example 1 and cleaned according to the method described in Example 3, was tested to measure the ability of the membrane to reduce metal concentration in PGMEA organic liquid (propylene glycol monomethyl ether acetate) under conditions of static soaking. The results demonstrate that said membrane was effective at removing metals, Al, B, Cr, Fe, Ni, and Zn in PGMEA. A solution was prepared by spiking PGMEA with a target metal concentration of 3000 ppt each of, Al, B, Cr, Fe, Ni, and Zn (PlasmaCAL Single Element Calibration Standards, SCP SCIENCE 1000 ppm) as an addition to metals that were already present in solution. Next, 20 mL of the PGMEA metal spiked organic liquid was added to the PTFE jar containing the IDA-modified UPE membrane disc prepared according to Example 1 and cleaned according to the method described in Example 3. The jar was capped and rotated for 16 hours. After 16 hours, the liquid was decanted into a clean PTFE vial for analysis. The metal concentration for the metal spiked PGMEA organic liquid, before and after exposure to the membrane, was measured by ICP-MS and used to calculate the metal removal efficiency of the membrane, as shown in Table 1.

TABLE 1

Metal reduction in PGMEA under static flow conditions

| Metal | % Metal Removal IDA modified UPE |
|---|---|
| Al | 100.0% |
| B | 99.6% |
| Cr | 100.0% |
| Fe | 100.0% |
| Ni | 99.9% |
| Zn | 100.0% |
| Total | 99.9% |

Example 4

Figure 2:
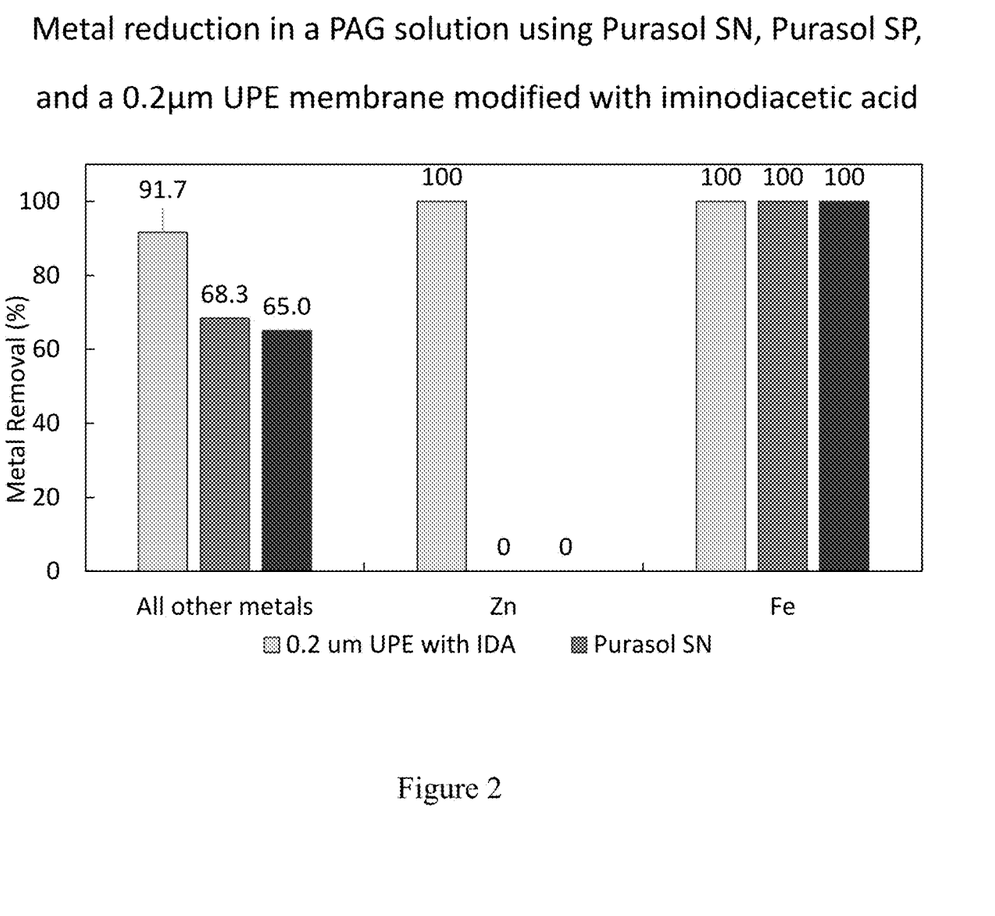
FIG. 2 is an illustration of the metal reduction in a photoactive generator (PAG) solution, comparing Purasol™ SN, Purasol™ SP filters (both from Entegris, Inc.), and a 0.2 µM UPE membrane modified with an iminodiacetic acid derivative.

Metal Reduction and Resulting Sensitivity Shift for a PAG Containing Solvent Mixture after Filtration with Purasol™ SN, Purasol™ SP, and UPE Membrane with IDA Ligand Membrane coupons of Purasol™ SN, Purasol™ SP and the 0.2 um pore size UPE modified with IDA (Example 1) were cleaned so that any contaminating metals were removed. A solvent mixture of PGMEA/ethyl lactate containing a photo-acid generator (PAG) was obtained and the metal concentration was determined to be 1.2 ppb of total metals. Each individual membrane coupon was challenged with the PAG containing solvent mixture and the filtrate was collected. The metal concentration in the filtrate was measured and the results show that all three of the membranes were able to remove 100% of Fe. Purasol™ SN and Purasol™ SP where ineffective at removing Zn, while the 0.2 um pore size UPE modified with IDA removed 100% of Zn. The 0.2 um pore size UPE modified with IDA removed >90% of all other metals, while, Purasol™ SN and Purasol™ SP removed 68.3 and 65.0% of all other metals respectively. The metal removal results are depicted in FIG. 2.

Figure 3:
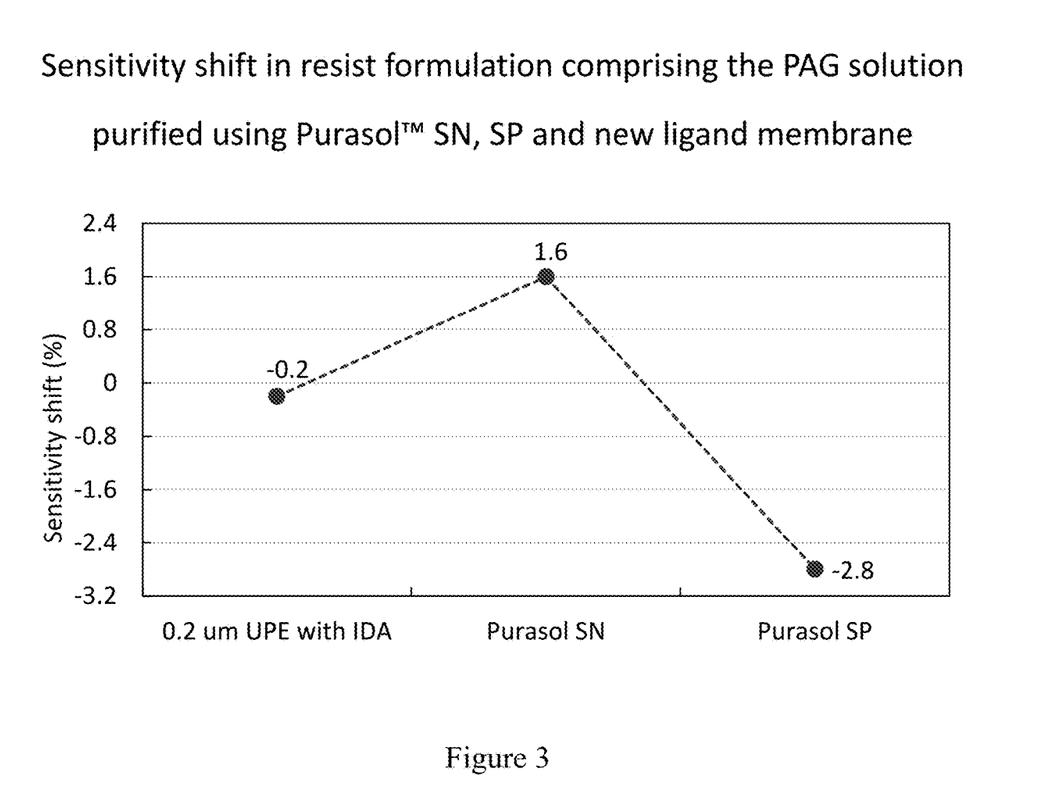
FIG. 3 is an illustration of the sensitivity shift in a photoresist formulation comprising a PAG solution comparing Purasol™ SN, Purasol™ SP filters (both from Entegris, Inc.), and a 0.2 µM UPE membrane modified with an iminodiacetic acid derivative.

Each filtered PAG solution was then reconstituted with polymer, quencher, surfactant and used to coat a silicon wafer that was exposed to UV light and developed to create patterns. The shift in the critical dimensions of the resulting features relative to patterns produced by a formulation of similar components, but with non-filtered PAG, was used to ascertain the impact of filtration on the photoacid generation efficiency. As depicted in FIG. 3, filtration of the PAG solution through Purasol™ SN and SP membranes resulted in a measurable change in the pattern size and a resulting sensitivity shift (%) of 1.6 and −2.8 respectively. As further depicted in FIG. 3, the sensitivity shift produced due to filtration with 0.2 um pore size UPE modified with IDA was only −0.2% indicating that filtration with this membrane had minimal impact on the performance of the formulation.

In a first aspect, a filter material comprises a polycarboxyl ligand, wherein the filter material is configured to be used in conjunction with a microelectronic fabrication system for providing a metal- or metal ion-depleted liquid composition and wherein the polycarboxyl ligands are covalently bound to the filter through at least one linkage which is other than through a carboxyl group.

A second aspect according to the first aspect, wherein the polycarboxyl ligand possesses the partial structure:

wherein x is an integer of from 1 to 6, n is equal to 2 or 3, and z represents either a zero or +1 valence.

A third aspect according to the first aspect, wherein the polycarboxyl ligand is derived from iminodiacetic acid, ethylenediamine tetraacetic acid, 1,2-cyclohexanediamine-N,N,N',N'-tetraacetic acid, nitriloacetic acid, or iminodisuccinic acid.

A fourth aspect according to any of the first, second, or third aspects, wherein the polycarboxyl ligand possesses the partial structure:

A fifth aspect according to any of the first through fourth aspects, wherein the filter material is a porous polymeric filter membrane comprising a polymeric material chosen from a polyamide, a polyimide, a polysulfone, a polyethersulfone, a polyolefin, a halogenated polymer, and a combination thereof.

A sixth aspect according to the fifth aspect, wherein the polymeric material is ultra-high molecular weight polyethylene.

A seventh aspect according to the fifth aspect, wherein the polymeric material is polytetrafluoroethylene.

In an eighth aspect, disclosed is a method of removing one or more metal(s) or metal ion(s) from a liquid composition, the method comprising: contacting a filter material with a liquid composition comprising one or more metal or metal ions, the filter material possessing polycarboxyl ligands, wherein the polycarboxyl ligands are covalently bound to the filter material through at least one linkage which is other than through a carboxyl group, and reducing an amount of the one or more metal or metal ions in the liquid composition.

A ninth aspect according to the eighth aspect, wherein the polycarboxyl ligand possesses the partial structure wherein x is an integer of from 1 to 6, n is equal to 2 or 3, and z represents either a zero or +1 valence.

A tenth aspect according to the eighth aspect, wherein the polycarboxyl ligand possesses the partial structure An eleventh aspect according to the eighth aspect, wherein the polycarboxyl ligand is derived from iminodiacetic acid, ethylenediamine tetraacetic acid, nitriloacetic acid, or iminodisuccinic acid.

A twelfth aspect according to any one of the eighth through eleventh aspects, wherein the filter material is a porous polymeric filter membrane comprising a polymeric material chosen from a polyamide, a polyimide, a polysulfone, a polyether-sulfone, a polyolefin, a halogenated polymer, and a combination thereof.

A thirteenth aspect according to the twelfth aspect, wherein the polymeric material is ultra-high molecular weight polyethylene.

A fourteenth aspect according to the twelfth aspect, wherein the polymeric material is polytetrafluoroethylene.

In a fifteenth aspect, disclosed herein is a composite membrane comprising:
a first filter material and a second filter material, an output facing surface of the first filter material in contact with an input facing surface of the second filter material,
wherein the first filter material or the second filter material possesses polycarboxyl ligands, wherein the polycarboxyl ligands are covalently bound to the filter through at least one linkage which is other than through a carboxyl group; and the second filter material is different from the first filter material, and wherein the composite membrane is configured to be used in conjunction with a microelectronic fabrication system for providing a metal- or metal ion-depleted liquid composition.

A sixteenth aspect according to the fifteenth aspect, wherein the polycarboxyl ligand has the partial structure wherein x is an integer of from 1 to 6, n is equal to 2 or 3, and z represents either a zero or +1 valence.

A seventeenth aspect according to the fifteenth aspect, wherein the polycarboxyl ligand has the partial structure

An eighteenth aspect according to any one of the fifteenth, sixteenth, or seventeenth aspects, wherein the first filter material, the second filter material, or both are a porous polymeric filter membrane comprising a polymeric material selected from the group consisting of a polyamide, a polyimide, a polysulfone, a polyether-sulfone, a polyolefin, a halogenated polymer, and a combination thereof.

A nineteenth aspect according to the fifteenth aspect, wherein the first filter material is a porous polymeric filter membrane and the second filter material is polymeric resin particles.

In a twentieth aspect, disclosed herein is a filter material comprising a porous polymeric filter material comprising ultra-high molecular weight polyethylene, having coated thereon a composition comprising the free-radical reaction product of (i) a polycarboxyl compound having an olefinic group and (ii) at least one monomeric, oligomeric, or polymeric compound having olefinic unsaturation.

A twenty-first aspect according to the twentieth aspect, wherein the polycarboxyl compounds are covalently bound to the filter through at least one linkage which is other than through a carboxyl group.

A twenty-second aspect according to the twentieth or twenty-first aspect, wherein the polycarboxyl compound having an olefinic group is a compound of the formula A twenty-third aspect according to the twentieth, twenty-first, or twenty-second aspect, wherein the at least one monomeric, oligomeric, or polymeric compound having olefinic unsaturation is chosen from N,N'-methylenebis(acrylamide), triethylene glycol dimethacrylate, triethylene glycol diacrylate, and ethylene glycol divinyl ether.

What is claimed is:
1. A filter material comprising a polycarboxyl ligand, wherein the filter material is configured to be used in conjunction with a microelectronic fabrication system for providing a metal- or metal ion-depleted liquid composition;
wherein the polycarboxyl ligands are covalently bound to the filter material through at least one linkage which is other than through a carboxyl group;

and wherein the filter material is modified by halogenation or haloalkylation to provide a surface-reactive chemistry for attachment of the polycarboxyl ligands if the filter material is not inherently amine-reactive.

2. The filter material of claim 1, the polycarboxyl ligand having the partial structure:

wherein x is an integer of from 1 to 6, n is equal to 2 or 3, and z represents either a zero or +1 valence.

3. The filter material of claim 1, wherein the polycarboxyl ligand is derived from iminodiacetic acid, ethylenediamine tetraacetic acid, 1,2-cyclohexanediamine-N,N,N',N'-tetraacetic acid, nitriloacetic acid, or iminodisuccinic acid.

4. The filter material of claim 1, the polycarboxyl ligand having the partial structure:

5. The filter material of claim 1, wherein the filter material is a porous polymeric filter membrane comprising a polymeric material selected from the group consisting of a polyamide, a polyimide, a polysulfone, a polyether-sulfone, a polyolefin, a halogenated polymer, and a combination thereof.

6. The filter material of claim 5, wherein the polymeric material is ultra-high molecular weight polyethylene.

7. The filter material of claim 5, wherein the polymeric material is polytetrafluoroethylene.

8. A composite membrane comprising:
a first filter material and a second filter material, wherein an output facing surface of the first filter material is in contact with an input facing surface of the second filter material, the first filter material or the second filter material comprising polycarboxyl ligands covalently bound to the filter through at least one linkage which is other than through a carboxyl group;
wherein the filter material comprising the polycarboxyl ligands is modified by halogenation or haloalkylation to provide a surface-reactive chemistry for attachment of the polycarboxyl ligands if the filter material is not inherently amine-reactive;
wherein the second filter material is different from the first filter material, and
wherein the composite membrane is configured to be used in conjunction with a microelectronic fabrication system for providing a metal- or metal ion-depleted liquid composition.

9. The composite membrane of claim 8, the polycarboxyl ligand having the partial structure wherein x is an integer of from 1 to 6, n is equal to 2 or 3, and z represents either a zero or +1 valence.

10. The composite membrane of claim 8, the polycarboxyl ligand having the partial structure 11. The composite membrane of claim 8, wherein the first filter material, the second filter material, or both are a porous polymeric filter membrane comprising a polymeric material selected from the group consisting of a polyamide, a polyimide, a polysulfone, a polyether-sulfone, a polyolefin, a halogenated polymer, and a combination thereof.

12. The composite membrane of claim 8, wherein the first filter material is a porous polymeric filter membrane and the second filter material is polymeric resin particles.

13. A filter material comprising a porous polymeric filter material comprising ultra-high molecular weight polyethylene, having coated thereon a composition comprising a free-radical reaction product of (i) a polycarboxyl compound having an olefinic group and (ii) at least one monomeric, oligomeric, or polymeric compound having olefinic unsaturation;
wherein the polycarboxyl compounds are covalently bound to the filter through at least one linkage which is other than through a carboxyl group.

14. The filter material of claim 13, wherein the polycarboxyl compound having an olefinic group is a compound of the formula 15. The filter of claim 13, wherein the at least one monomeric, oligomeric, or polymeric compound having olefinic unsaturation is chosen from N,N'-methylenebis (acrylamide), triethylene glycol dimethacrylate, triethylene glycol diacrylate, and ethylene glycol divinyl ether.

16. A method of removing one or more metals or metal ions from a liquid composition, the method comprising:
contacting a filter material with a liquid composition comprising one or more metals or metal ions, the filter material comprising polycarboxyl ligands covalently bound to the filter material through at least one linkage which is other than through a carboxyl group, wherein the filter material is modified by halogenation or haloalkylation to provide a surface-reactive chemistry for attachment of the polycarboxyl ligands if the filter material is not inherently amine-reactive,
and
reducing an amount of the one or more metal or metal ions in the liquid composition.

17. The method of claim 16, the polycarboxyl ligand having the partial structure wherein x is an integer of from 1 to 6, n is equal to 2 or 3, and z represents either a zero or +1 valence.

18. The method of claim 16, the polycarboxyl ligand having the partial structure 19. The method of claim 16, wherein the filter material is a porous polymeric filter membrane comprising a polymeric material selected from the group consisting of a polyamide, a polyimide, a polysulfone, a polyether-sulfone, a polyolefin, a halogenated polymer, and a combination thereof.

* * * * *